United States Patent
Larson et al.

(10) Patent No.: US 7,849,738 B2
(45) Date of Patent: Dec. 14, 2010

(54) DEVICE FOR DETECTING INTERACTION WITH AN OBJECT

(75) Inventors: Bradley James Larson, Madison, WI (US); Joerg Werner Baier, Verona, WI (US)

(73) Assignee: Sonoplot, Inc., Middleton, WI (US)

( * ) Notice: Subject to any disclaimer, the term of this patent is extended or adjusted under 35 U.S.C. 154(b) by 728 days.

(21) Appl. No.: 11/716,097

(22) Filed: Mar. 9, 2007

(65) Prior Publication Data

US 2007/0210677 A1 Sep. 13, 2007

Related U.S. Application Data

(60) Provisional application No. 60/781,777, filed on Mar. 13, 2006.

(51) Int. Cl.
*G01F 23/28* (2006.01)
(52) U.S. Cl. .................................... 73/290 V
(58) Field of Classification Search ............... 73/290 R, 73/290 V, 314
See application file for complete search history.

(56) References Cited

U.S. PATENT DOCUMENTS

| | | | |
|---|---|---|---|
| 4,307,610 A | 12/1981 | Leupp et al. | |
| 4,540,981 A | 9/1985 | Lapetina et al. | |
| 4,790,183 A * | 12/1988 | Pfost et al. | 73/290 V |
| 4,864,856 A | 9/1989 | Ichikawa et al. | |
| 5,533,398 A * | 7/1996 | Sakurai | 73/573 |
| 6,094,971 A | 8/2000 | Edwards et al. | |
| 6,774,626 B2 * | 8/2004 | Abe | 324/210 |
| 6,781,287 B1 | 8/2004 | Dam et al. | |
| 6,874,699 B2 | 4/2005 | Larson et al. | |
| 7,685,733 B2 * | 3/2010 | Ohmori et al. | 33/559 |

OTHER PUBLICATIONS

Konakawa, JP2003121459, Oct. 2001.*

* cited by examiner

*Primary Examiner*—Hezron Williams
*Assistant Examiner*—Alex Devito
(74) *Attorney, Agent, or Firm*—Casimir Jones SC

(57) ABSTRACT

A device and method for the detection of the interaction between two or more objects is disclosed. The device utilizes electrical impedance spectra measured from a piezoelectric element attached to one such object. Comparison of such spectra along a range of traverse allows precise estimates of distance to be made. One useful application is the topographical mapping of a surface.

8 Claims, 5 Drawing Sheets

DEVICE FOR DETECTING INTERACTION WITH AN OBJECT

CROSS-REFERENCE TO RELATED APPLICATION

This application claims priority from a Provisional Application of the same title filed Mar. 13, 2006, Ser. No. 60/781,777.

BACKGROUND OF THE INVENTION

Detecting and measuring the point of contact between two or more objects has many applications. In many fluid dispensing systems, it is desirable to maintain a constant distance between the dispenser and the surface to ensure a uniform deposition of fluid. A particular example of this is in the fabrication of biological microarrays, where thousands of small spots (on the order of 50-250 microns in diameter) of biological molecules are placed at precise locations on a chemically treated surface. The more uniform the shape and size of the spots on a microarray, the more reliable results obtained from it in an experimental or diagnostic capacity. An example of a fluid dispenser for manufacturing microarrays is disclosed in U.S. Pat. No. 6,874,699.

Uniform dispensing can be a challenge when the target surfaces have imperfections or are not perfectly level. The larger the area dispensed on, the harder it is to maintain a constant distance between the dispenser and the surface.

An elementary contact sensing device comprises an object moved in relation to another, recording the distance of travel, and the contacting event, and then calculating the distance from the point of origin to the point of contact. The contact event may be indicated by closing an electric circuit where the contact and target objects are electrical conductors. Other methods of detection measure other electrical properties such as impedance, resistance, capacitance, or phase.

Certain materials called piezoelectrics will expand or contract when exposed to an electrical potential, and will also generate an electric potential when deformed. By applying an alternating current to a piezoelectric element, it can be made to vibrate. Impedance can be used as an electrical measure of the mechanical response of piezoelectric element to a specific frequency of alternating current. By measuring impedance as a function of frequency, the vibrational response of a piezoelectric element can be observed. The impedance spectrum generated by scanning frequencies at discrete intervals provides a unique fingerprint of the vibrational properties of a piezoelectric element that will change with alterations in the element's environment, such as materials to which it is attached or to which it comes into contact.

There have been several applications developed which take advantage of changes in impedance spectra to detect changes in material properties at remote sites. For example, U.S. Pat. No. 4,307,610 discloses a method for measuring crack propagation in materials undergoing alternating stress. An alternating load is applied to a pre-cracked specimen, and the change in frequency response is registered. The load is applied as a high frequency pulsator having an air gap between two poles, one mounted on the sample. The piezoelectric element functions to convert mechanical signals into electrical signals. U.S. Pat. No. 6,094,971 describes a scanning-probe microscope in which a resonating piezoelectric element drives a tuning fork oscillator which vibrates a cantilever at a position close to the surface of a sample. When the cantilever comes into tapping contact with the surface, there is a decrease in oscillation amplitude and change in the impedance measured from the piezoelectric element. In this application, piezo-induced vibration is calibrated to a single pre-determined frequency.

In U.S. Pat. No. 4,540,981, a vibratory device for detecting liquid levels utilizes a piezoelectric element to transmit vibrations to a metal rod suspended in a liquid reservoir. Vibration is established over a range of frequencies to ensure that the rod is vibrated at its resonance frequency. As the rod is immersed in fluid, its vibration at resonance will be damped, providing an indication of a liquid level in a reservoir. U.S. Pat. Nos. 4,864,856 and 6,781,287 describe other such liquid level sensing devices also incorporating a piezoelectric element.

SUMMARY OF THE INVENTION

It is an object of the present invention to provide a device which senses the distance of travel from a starting position to the point of contact on a substrate surface. It is a further object to repeat sensing at a series of substrate positions to map the topography of the surface, so that adjustments to the height from the dispenser to the substrate can be automatically made to compensate for surface imperfections or deviations from flatness. In a still further object, the present sensing means can be used to measure the incremental increase or decrease in liquid contained within a dispenser as it fills or empties.

In accordance with the present invention, a device for detecting interaction of two or more objects utilizes a contact object and a piezoelectric element attached thereto. The piezoelectric element is selected to have a measurable change in electrical properties at more than one applied current frequency when the contact object interacts with another object or objects. The device has an operable electrical connection for measuring electrical properties of the element such as impedance, resistance, capacitance, reactance, and phase. This portion of the device is mounted on positioning means, which move the contact object into proximity with a target object. The target object may be a planar substrate such as a substantially planar object, a curved object, an object with a patterned or complex surface, or a spatially disposed object. Physical interaction between the contact and target objects may be actual physical contact or a bridging event, such as a liquid droplet poised between a dispenser tip and a substrate. An appropriate contact object is chosen that yields a significant change in the piezoelectric element's impedance at multiple frequencies when a contact or bridging event occurs. The contact object may be a hollow glass cylinder having a tapered tip, a solid metal pin, a hollow metal cylinder having a tapered tip, or combinations thereof.

In one method of the present invention for calibrating detection of the physical interaction of two or more objects, a contact object is attached to a piezoelectric element having an operable electrical connection to means for measuring the electrical properties of the element. The contact object is mounted on a positioning device which may be directed incrementally in at least one, and preferably along three axes in a substantially rectilinear path of traverse. An initial calibration is performed, starting with a target object being placed in the path of traverse without coming into contact with the contact object, and then measuring an impedance spectrum of the piezoelectric element and recording it. The contact object is then advanced along the path of traverse until physical interaction occurs between the contact object and the target object or objects. Physical interaction may be direct contact, creation of a liquid bridge between the contact and target objects, or insertion of the dispenser into a fluid well.

An impedance spectrum of the piezoelectric element is measured again, and the spectra for these two conditions are stored electronically.

After this calibration has been performed once for a given dispenser, it may be used to sense the location of a surface. To do this, the contact object is advanced incrementally along the path of traverse, with impedance measurements taken at each position. These measurements are compared to the calibration spectra, with the closest fit identifying the state of the contact sensor. In effect, the electrical properties are compared with previously calibrated values to determine when interaction between the contact object and the target object has occurred. When interaction is observed, movement of the contact object is reversed along the path of traverse. Retreat from the point of interaction is made in smaller increments than the advancing increments to fine tune the point of disengagement of the contact object from interaction with the target object. In each case the electrical properties are again compared with previously calibrated values to determine when interaction between the contact object and target object is no longer occurring. The steps of this method may be repeated a plurality of times at different locations on a substrate. The differences in the path length of each traverse may then be correlated to produce a topological map of surface imperfections in a target surface, and also determine the cant of a substantially flat substrate.

The principle of the present invention can be applied in a device for detecting the fluid level in a hollow vessel. A hollow substantially round tubular structure is adapted to contain a liquid, such as a capillary tapered at one end. A piezoelectric element is attached to the outer wall of the tubular structure which is connected to an operable electrical interface to means for measuring the electrical properties of the element. Measurements of the impedance spectrum at more than one applied alternating current frequency of the piezoelectric element are made as the liquid level is changed by incremental filling or draining volumes of liquid contained in the tubular structure. The changes in impedance can be correlated to the volumes so filled or drained. This has particular application in fluid dispensing to monitor the deposition of droplets.

DESCRIPTION OF THE PREFERRED EMBODIMENTS

Figure 1A:
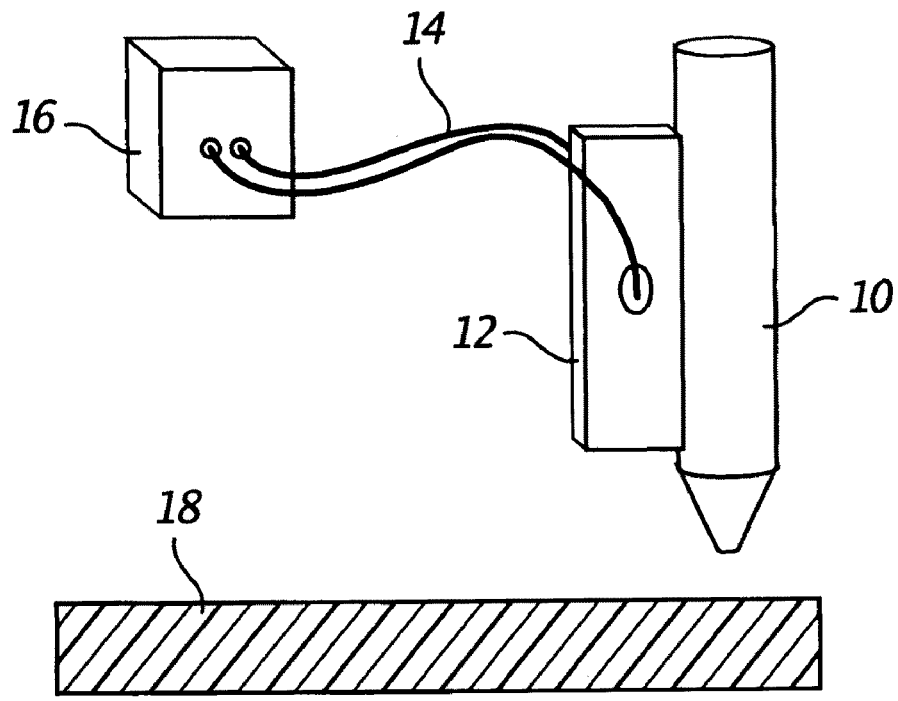
FIG. 1A is a schematic representation of the components of this invention, demonstrating a contact object attached to a piezoelectric element, with an electrical connection to a device capable of making electrical measurements of the piezoelectric, such as electrical impedance. In this illustration, the contact object is shown at a distance from another solid object.
Figure 1B:
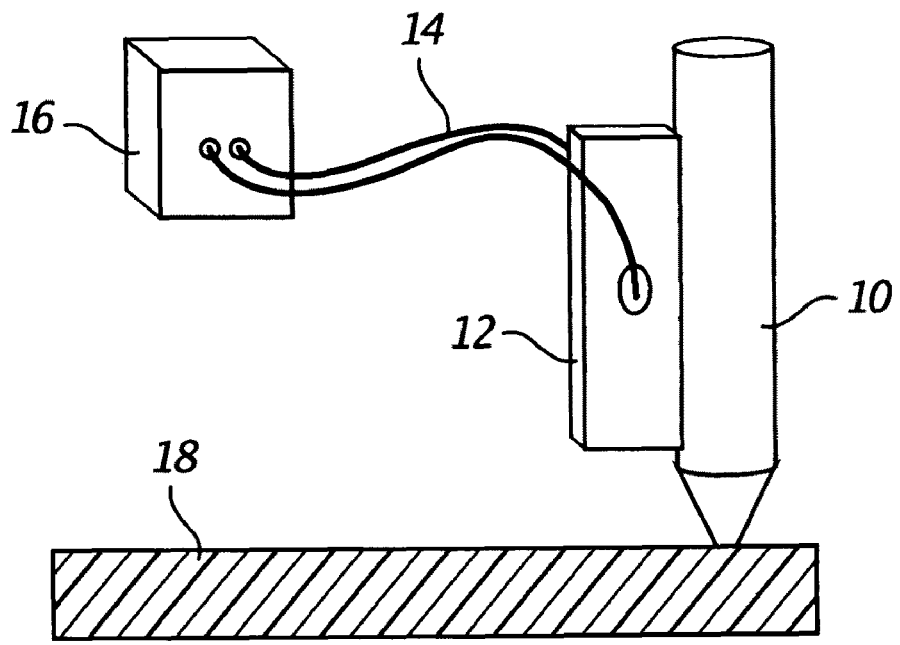
FIG. 1B is a schematic of the same invention depicted in FIG. 1A, but in this case the contact object is shown physically interacting with another solid object.

A schematic diagram of a preferred embodiment of the present invention is set forth in FIG. 1A and FIG. 1B. In this embodiment, the impedance of a piezoelectric element 12 is measured as a function of frequency of applied alternating current by an impedance analyzer 16 attached to the piezoelectric element by wires 14. This impedance spectrum is distinctive for the mass, shape, and composition of the object to which the piezoelectric is attached. A number of different types of piezoelectric elements can be adapted to this application. Common types include $BaTiO_3$, $PbZrO_3$, and $PbTiO_3$. A lead zirconate titanate (PZT) piezoelectric is preferred. While the shape and mass of the piezoelectric element influence its impedance properties and resonance frequencies, it is satisfactory for practice of the invention to utilize a small rectangular piece bonded by adhesive perpendicularly to the shaft of a contact object 10. Alternatively, the piezoelectric element may be formed as a collar around the contact object.

Interaction with a solid surface 18 or other material induces a change in the vibrational properties of the contact object, which leads to a change in the impedance spectrum of the attached piezoelectric element.

The contact object may be virtually any shape and composed of a variety of materials, including glass, metal, polymers, and ceramics, including a hollow glass capillary or cylinder, a tapered hollow glass cylinder, a recessed metal pin, and a solid metal pin. Hollow glass capillaries or thin metal rods are preferred. The shape is largely dictated by the nature of the target object. For example, a very thin contact object would be required if the objective is to topologically map the bottom surface of a well in a 96 well plate. In general, for impedance measurements there is a greater sensitivity observed for contact objects of lesser mass, so that a hollow capillary is more sensitive in detecting physical interaction with a target object than a metal rod of the same diameter.

Figure 2A:
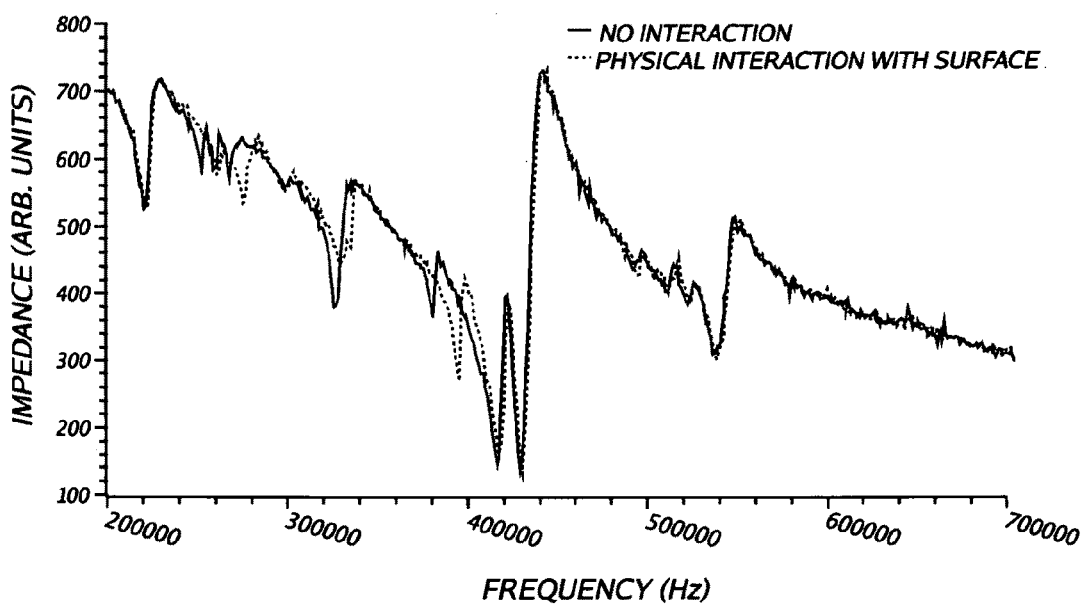
FIG. 2A is an overlay of two impedance spectra gathered from a piezoelectric attached to a contact object when that object is at a distance from a solid surface and in contact with a solid surface.
Figure 2B:
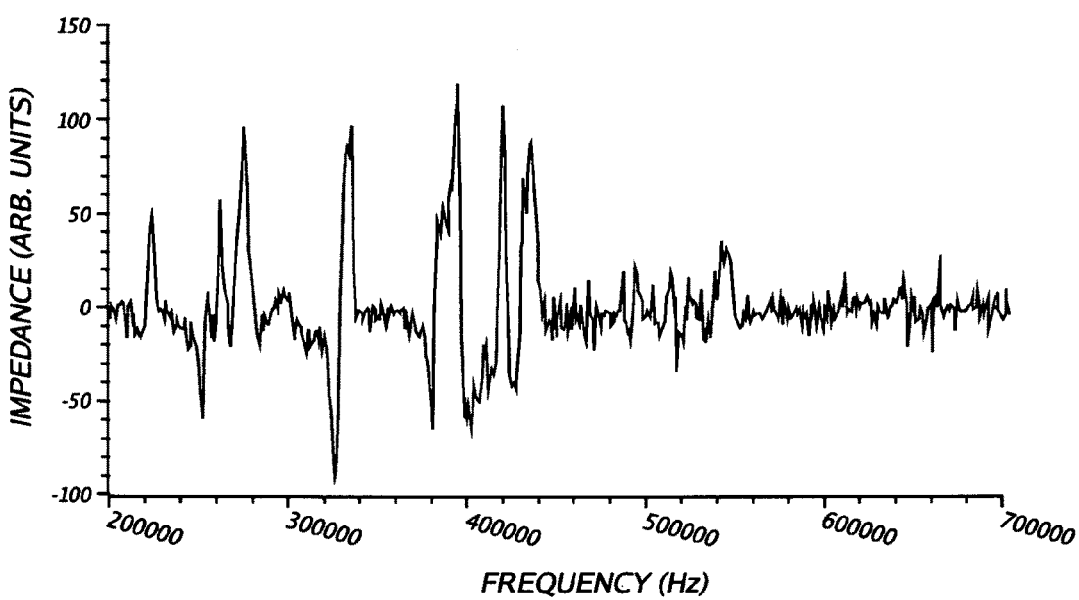
FIG. 2B is a plot of the difference between the two spectra in FIG. 2B.

FIG. 2A shows an overlay of two impedance spectra gathered with a contact object hanging freely in space and with the contact object physically touching a solid surface. The solid line indicates the capillary in air, and the dotted line indicates the same capillary in contact with a glass substrate. The differences between the two spectra are plotted in FIG. 2B. The points of greatest divergence in impedance spectra as between interaction and no interaction tend to be at or near the resonance frequencies of the piezoelectric element and contact object assembly (where electrical impedance of the piezoelectric goes from a local minimum to a local maximum), although comparison of impedance spectra is useful even for materials that resonate poorly. Not all impedance values are changed as a result of physical interaction with target, and many changes are very small.

Figure 3A:
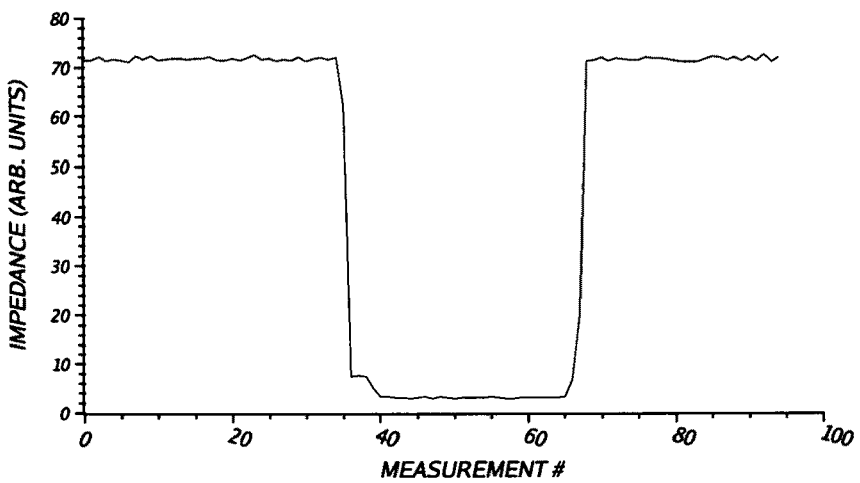
FIG. 3A shows the sum of the difference in impedance at five frequencies, as a function of time, between the measured value and a previously calibrated value.

Comparison of impedance at as few as a single frequency is sufficient to distinguish interaction from no interaction, but the reliability of measurements improves with comparisons of impedance at several frequencies. FIG. 3A shows data from interaction sensing wherein a hollow glass capillary approaches a flat glass surface, contacts it, and then withdraws. The sum of the differences in impedance at five frequencies, between a current measurement and known values for when the contact object is touching the surface, are plotted for samples taken at regular time intervals.

Figure 3B:
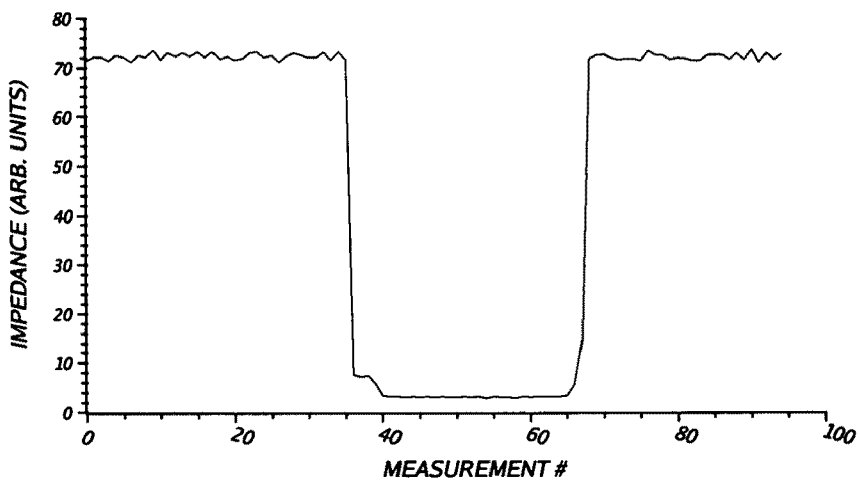
FIG. 3B shows the sum of the difference in impedance at three frequencies, under the same conditions as for FIG. 3A.
Figure 3C:
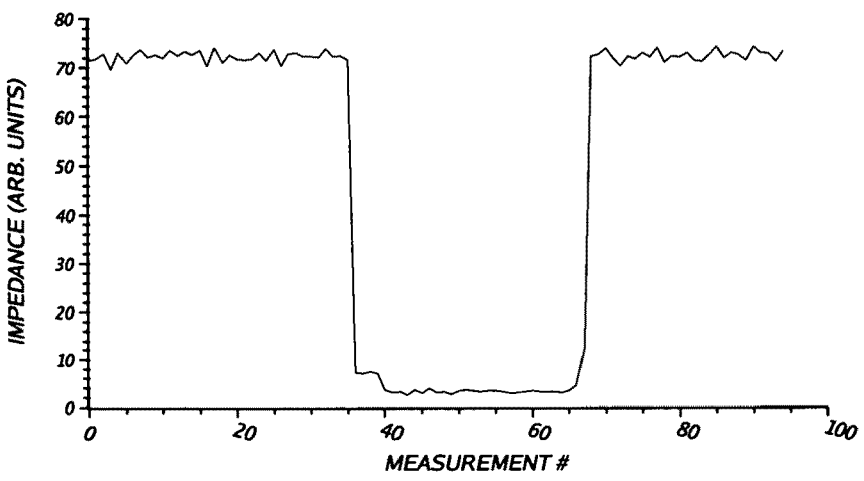
FIG. 3C shows the sum of the differences in impedance at one frequency, under the same conditions as for FIG. 3A.

FIG. 3B and FIG. 3C show the same set of measurements, only with three frequencies and one frequency being measured, respectively. A reduction in the number of frequencies tested against reduces the signal to noise ratio for the detection of an interaction event, as summarized in Table 1 for this particular set of measurements.

TABLE 1

| Number of Frequencies Measured | Signal-to-noise Ratio |
|---|---|
| 5 | 199 |
| 4 | 160 |
| 3 | 106 |
| 2 | 88 |
| 1 | 64 |

These electrical impedance measurements can be conducted over a wide range of frequencies, from less than 1 kHz to greater than 3000 kHz, but the range 200-1500 kHz is practical for use with millimeter-scale PZT piezoelectric elements.

The target object can also be of any shape, density, and composition. However, it is anticipated that because the invention has particular application in the field of microarrays, the most typical target object will be a microarray substrate. These are generally flat glass, metal or ceramic sheets, which may be chemically functionalized, or coated with reflective, hydrophobic, or optically conductive layers. They may be porous so that individual mapping points may be spatially disposed. If there is a cant to the substrate, it has an angular surface structure, detectable by topographic sampling. Some substrates such as hydrogels or fine membranes are very delicate and easily damaged by spotting pins or other objects which strike the surface. The incremental probing technique of the present invention prevents or minimizes such damage, and represents a novel approach to topologically mapping the surface of substrates which only permit non-contact deposition of micro-spots or line features.

In order to change the position of the contact object relative to a target object, it is necessary to have positioning means which engage the contact object and direct its movement in at least one dimension. If multiple points of analysis are desired, as in the topological mapping of a two dimensional surface, then a three dimensional positioning device is needed to maintain alignment for data comparison.

There are many commercial positioning devices on the market suitable for practice of the present invention. Any system capable of accurate movement is satisfactory, but a unit capable of accurate movement in an X,Y plane of +/−10 micron increments, and 1 micron increments in the Z axis is preferred. One such system, developed and sold by Telechem International, employs a floating print head, which ensures that the spotting pin and underlying substrate will not be damaged if the path of traverse of the pin exceeds the distance to the surface of the substrate. This configuration is ideal for practice of the present invention, in that incremental advance by 10-30 micron intervals of the contact object to a position slightly greater than the contact point will not damage the object or target. The contact object can then be retracted by incremental 1 micron intervals to obtain a precise measure of the distance at which contact is broken.

Figure 4A:
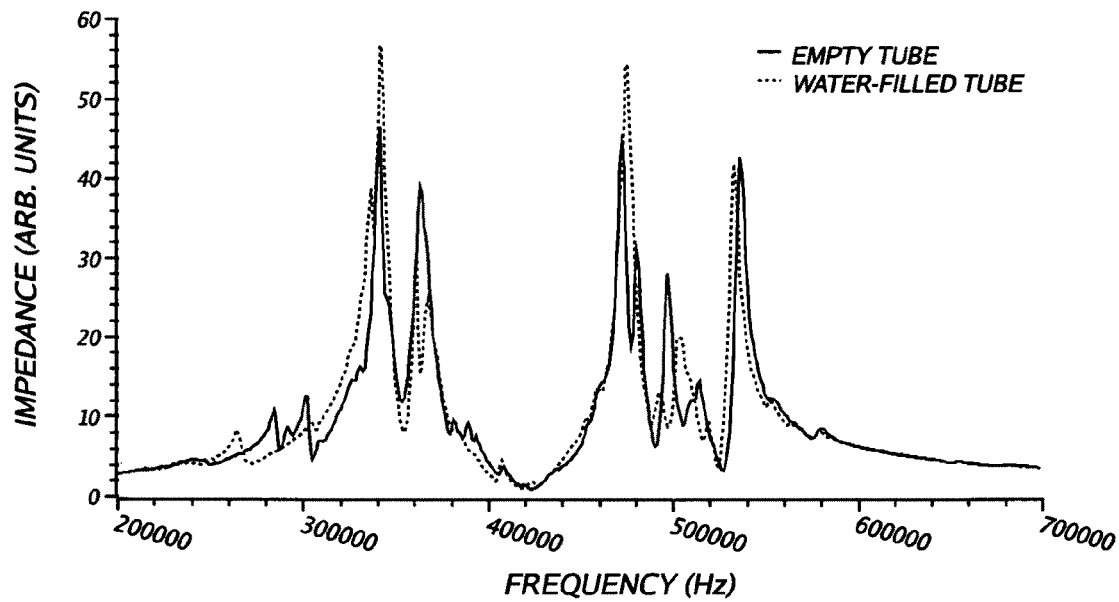
FIG. 4A is an overlay of two impedance spectra gathered from a piezoelectric element attached to a hollow tube when that tube is empty and when it is full of water.
Figure 4B:
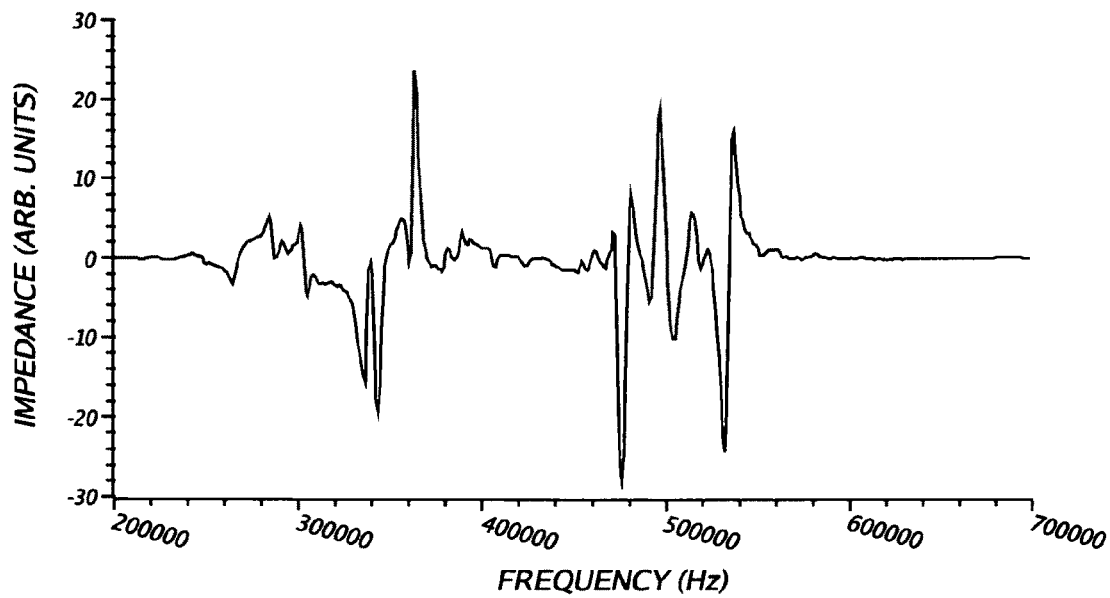
FIG. 4B is a plot of the difference between the two spectra in FIG. 4A.

FIG. 4A illustrates the embodiment of monitoring fluid filling of a hollow vessel. The solid line shows the impedance spectrum corresponding to an empty vessel, and the dotted line shows the shift in spectrum resulting from filling the vessel with water. FIG. 4B plots the difference between the impedance values of the two scans. As the vessel fills, the measured impedance spectrum grows closer to that of the filled vessel and becomes significantly different from the calibration scan of the empty vessel.

Example 1

This example demonstrates the use of impedance-based surface contact detection to determine the height of a solid surface relative to the tip of a fluid dispenser acting as the contact object. A dispenser, consisting of a hollow pulled-glass micropipette attached to a rectangular piece of PZT piezoelectric, was mounted to a robotic positioning stage. The stage had a resolution of 1 micron. The movement of the stage was controlled via a drive connected to a personal computer (PC). The dispenser had two electrical leads which were wired into an impedance analyzer.

The dispenser was calibrated by first measuring the magnitude of the electrical impedance at 800 discrete frequencies, starting at 200 kHz and increasing in 1 kHz steps up to 1000 kHz, for the dispenser suspended freely in the air. The dispenser was then moved until it was in physical contact with a glass slide. The same impedance measurement at various frequencies was performed while the dispenser contacted the surface of the slide. The impedance scans taken at these two conditions were saved on a PC and software running on it was able to isolate five frequencies at which the greatest difference between the two conditions occurred. This calibration process needs to be performed only once for a given contact object.

To start the surface detection process, the dispenser was first retracted from the surface. The software then scanned the five frequencies identified in the calibration process and determined if the impedance values measured approximated the spectrum of either of the two conditions. If the in-air condition more closely matched the measured values, the dispenser was advanced 10 microns closer to the surface. This measure-and-move procedure was repeated until contact with the surface was indicated. The dispenser was then retracted at 1 micron increments until contact was broken. By keeping track of the number and size of movements, and the absolute coordinate of the positioning stage, the software was then able to calculate the exact position of the surface, relative to the tip of the dispenser.

Typical feedback from the sensing operation is provided in FIG. 3A, where the sum of the differences in impedance between the surface contact calibration impedance scan and the currently measured values at five points is plotted for each positioning stage movement. Initially, a large difference is observed as the dispenser is hanging freely at a distance from the surface. When contact has been made between the dispenser tip and the surface, the difference in impedance drops sharply. This difference rises sharply after the dispenser has been pulled away from the surface.

Example 2

This example demonstrates the use of surface height detection to measure the cant of a flat surface as part of a calibration procedure. A dispenser, of the type used in Example 1, was attached to a robotic positioning system capable of moving the dispenser in three axes (X, Y, and Z). The dispenser was connected to an impedance analyzer, and the positioning system was connected to a PC running software that monitored and controlled it. Impedance measurements and controlled movements of the Z axis were used to determine the position of the surface relative to the dispenser tip, as in Example 1. The surface height at this point was recorded and the dispenser was retracted. The X axis positioner then moved the dispenser a pre-set distance along the surface, and surface height detection was again performed. This procedure was repeated at five evenly spaced sites along the X axis, and at five evenly spaced sites along the Y axis. In each direction, the five points were fit using least-squares regression analysis to calculate the slope of the surface in that axis. Combining the slopes from both axes, the overall cant of the flat surface was determined.

Example 3

Figure 5:
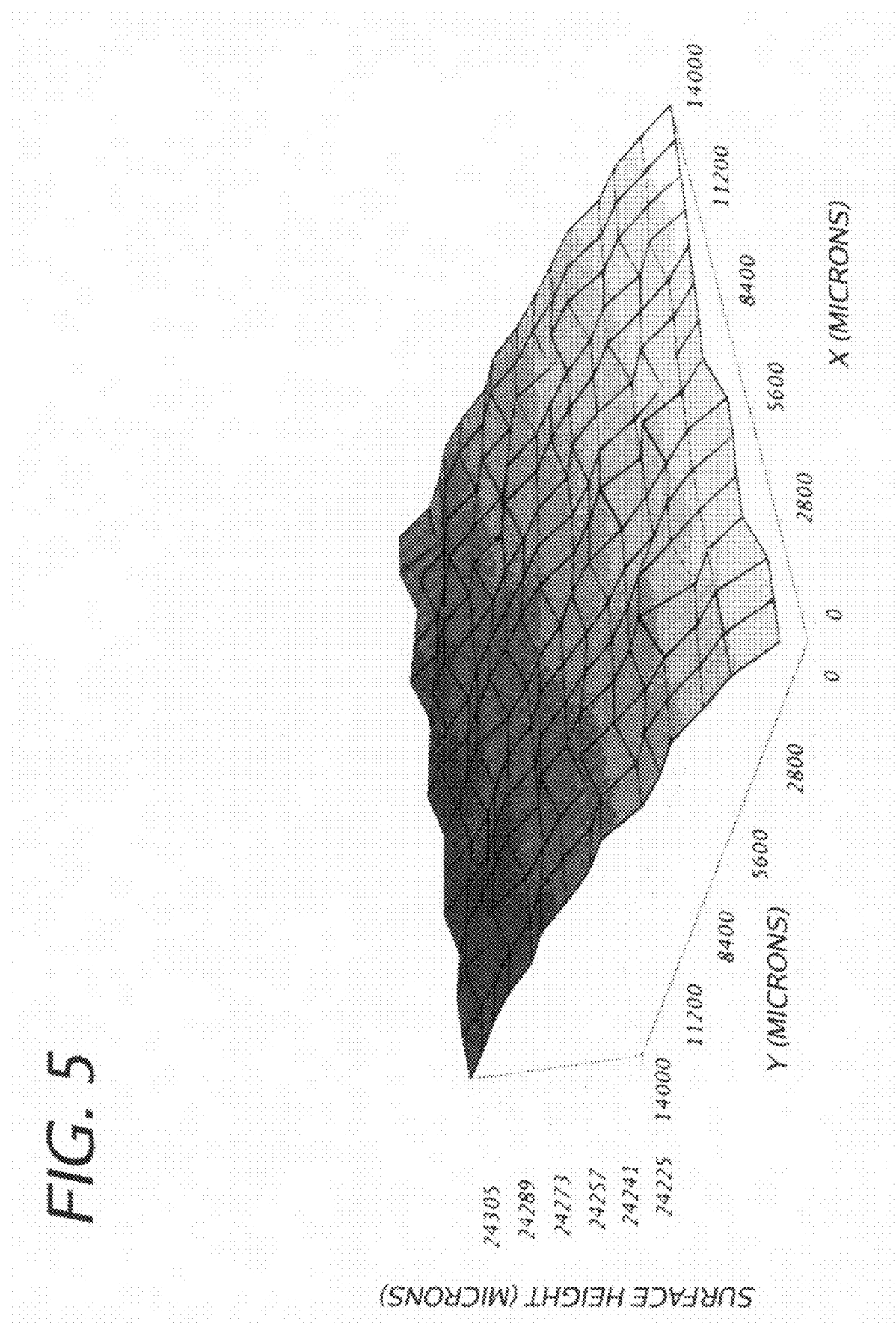
FIG. 5 is a contour plot of the topography of a surface as measured by this invention when mounted on a precision positioning system.

This example demonstrates the use of surface height measurements to determine the shape or topography of an irregular surface by mapping a grid of locations. The same procedure was implemented as in Examples 1 and 2, only a grid of surface locations is examined. The surface height is measured at a series of points evenly spaced in the X direction, then the Y axis is moved a pre-set distance and the series of X measurements of taken again. This is repeated until an entire grid of surface heights has been measured. Each of these heights, and its corresponding X, Y coordinate was stored on the controlling computer and assembled as a topographic image, shown representatively in FIG. 5.

What is claimed is:

1. A method of calibrating the detection of the physical interaction of two or more objects comprising:
    attaching a piezoelectric element to a contact object having an operable electrical connection to means for measuring the electrical properties of said element;
    mounting said contact object on a positioning device whereby the position of said contact object can be directed incrementally in at least one dimension along a substantially rectilinear path of traverse;
    placing a target object in the path of traverse of said contact object;
    measuring the electrical properties of said piezoelectric element at more than one applied alternating current frequency without interacting said contact object with said target object and recording those properties;
    advancing said contact object along the path of traverse until interaction occurs between said contact object and said target object; and
    measuring the electrical properties of said piezoelectric element while said contact object is interacting with said target object and recording those properties.

2. The method of claim 1, wherein said physical interaction is physical contact between said contact object and said target object.

3. The method of claim 1, wherein said physical interaction is a liquid bridge between said contact object and said target object.

4. A method of detecting the physical interaction physical interaction of two or more objects comprising:
    attaching a piezoelectric element to a contact object having an operable electrical connection to means for measuring the electrical properties of said element;
    mounting said contact object on a positioning device whereby the position of said contact object can be directed incrementally in at least one dimension along a substantially rectilinear path of traverse;
    advancing said contact object incrementally along the path of traverse in the direction towards said target object;
    measuring the electrical properties of said piezoelectric element at each such incremental position; and
    comparing the electrical properties with previously calibrated values to determine when interaction between said contact object and target object has occurred.

5. The method of claim 4, wherein said physical interaction is physical contact between said contact object and said target object.

6. The method of claim 4, wherein said physical interaction is a liquid bridge between said contact object and said target object.

7. The method of claim 4 wherein the steps thereof are carried out a plurality of times at different locations on a substrate, whereby to topologically map surface imperfections and determine cant of the substrate.

8. The method of claim 4, further comprising the steps of:
    on interaction of the contact object and target object, reversing the direction of path traverse of said contact object;
    retreating from the point of interaction incrementally in smaller increments than the advancing increment; and
    comparing the electrical properties with previously calibrated values to determine when interaction between said contact object and target object is no longer occurring.

* * * * *